United States Patent
Mahadevan et al.

(10) Patent No.: US 10,682,092 B2
(45) Date of Patent: Jun. 16, 2020

(54) SYSTEM AND METHOD FOR DETECTING SLOW WAVES

(71) Applicant: KONINKLIJKE PHILIPS N.V., Eindhoven (NL)

(72) Inventors: Anandi Mahadevan, Murrysville, PA (US); William Anthony Truschel, Oakmont, PA (US); Jesse Salazar, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 401 days.

(21) Appl. No.: 15/514,919

(22) PCT Filed: Sep. 21, 2015

(86) PCT No.: PCT/IB2015/057248
§ 371 (c)(1),
(2) Date: Mar. 28, 2017

(87) PCT Pub. No.: WO2016/051305
PCT Pub. Date: Apr. 7, 2016

(65) Prior Publication Data
US 2017/0215789 A1    Aug. 3, 2017

Related U.S. Application Data

(60) Provisional application No. 62/057,654, filed on Sep. 30, 2014.

(51) Int. Cl.
*A61B 5/00* (2006.01)
*A61B 5/04* (2006.01)
(Continued)

(52) U.S. Cl.
CPC ............ *A61B 5/4812* (2013.01); *A61B 5/048* (2013.01); *A61B 5/04012* (2013.01);
(Continued)

(58) Field of Classification Search
None
See application file for complete search history.

(56) References Cited

U.S. PATENT DOCUMENTS

| 2013/0123584 A1 | 5/2013 | Sun et al. |
| 2014/0057232 A1 | 2/2014 | Wetmore et al. |

OTHER PUBLICATIONS

Picot et al., 2012, Detection of Cortical Slow Eaves in the Sleep EEG Using a Modified Matching Pursuit Method with a Restricted Dictionary, IEE Transactions on Biomedical Engineering, vol. 59, No. 10, pp. 2808-2817. (Year: 2012).*
(Continued)

*Primary Examiner* — Michael R Bloch

(57) ABSTRACT

The present disclosure pertains to a system configured to detect slow waves in a subject during a sleep session. The system generates output signals conveying information related to brain activity of the subject. The system is configured to detect individual sleep stages of the subject, the individual sleep stages including a deep sleep stage; and, responsive to detecting the deep sleep stage, generate a harmonic representation of the output signals for a period of time during the sleep session that includes the deep sleep stage; identify two or more points of significance on the harmonic representation of the output signals; and analyze a shape of the harmonic representation of the output signals around the two or more points of significance to determine whether the shape of the harmonic representation of the output signals around the two or more points of significance corresponds to a shape of a slow wave.

12 Claims, 5 Drawing Sheets

(51) Int. Cl.
*A61B 5/048* (2006.01)
*A61M 21/02* (2006.01)
*A61M 21/00* (2006.01)

(52) U.S. Cl.
CPC ........... *A61B 5/7235* (2013.01); *A61M 21/02* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2230/10* (2013.01)

(56) References Cited

OTHER PUBLICATIONS

Menicucci et al., 2009, Functional Structure of Spontaneous Sleep Slow Oscillation Activity in Humans, PLoS ONE, vol. 4, No. 10, pp. 1-11 (Year: 2009).*
Picot et al, "Detection of Cortical Slow Waves in the Sleep EEG Using a Modified Matching Pursuit Method With a Restricted Dictionary", IEEE Transactions on Biomedical Engineering, vol. 59, No. 10, 2012, pp. 2808-2817.
Massimini, "The Sleep Slow Oscillation as a Braveling Wave", Journal of Neuroscience, vol. 24, No. 31, pp. 6862-6870.
Picot et al, "Automated Detection of Sleep EEG Slow Waves Based on Matching Pursuit Using a Restricted Dictionary", Engineering in Medicine and Biology Society, 2011, pp. 4824-4827.

* cited by examiner

US 10,682,092 B2

SYSTEM AND METHOD FOR DETECTING SLOW WAVES

CROSS-REFERENCE TO PRIOR APPLICATIONS

This application is the U.S. National Phase application under 35 U.S.C. § 371 of International Application Serial No. PCT/IB2015/057248, filed on Sep. 21, 2015, which claims the benefit of U.S. Application Ser. No. 62/057,654, filed on Sep. 30, 2014. These applications are hereby incorporated by reference herein.

BACKGROUND

1. Field

The present disclosure pertains to a system and method for detecting slow waves in a subject during a sleep session.

2. Description of the Related Art

Systems for monitoring sleep are known. Determining sleep stages during sleep is known. Systems to detect slow waves during deep sleep are known. Slow waves are electrical impulses of the neurons in the brain. Slow waves are typically detected based on an electroencephalogram (EEG) signal. Research has shown that memory is enhanced when an auditory stimulus is provided immediately following the detection of a slow wave. An auditory stimulus out of phase with a slow wave may suppress slow wave activity. Various researchers have tried different methods to detect slow waves and then fit fixed time interval stimulation to the detected slow waves. A problem with using fixed time intervals is that slow waves change in frequency and fixed time interval stimulation may cause an auditory stimulus to be provided at a time instance that does not correspond to a slow wave and unintentionally suppress slow wave activity.

SUMMARY

Accordingly, one or more aspects of the present disclosure relate to a system configured to detect slow waves in a subject during a sleep session. The system comprises one or more sensors, one or more physical computer processors, and/or other components. The one or more sensors are configured to generate output signals conveying information related to brain activity of the subject. The one or more physical computer processors are configured by computer-readable instructions to detect individual sleep stages of the subject during the sleep session based on the output signals, the individual sleep stages including a deep sleep stage; and, responsive to detecting the deep sleep stage, generate a harmonic representation of the output signals for a period of time during the sleep session that includes the deep sleep stage; identify two or more points of significance on the harmonic representation of the output signals; and analyze a shape of the harmonic representation of the output signals around the two or more points of significance to determine whether the shape of the harmonic representation of the output signals around the two or more points of significance corresponds to a shape of a slow wave.

Another aspect of the present disclosure relates to a method for detecting slow waves in a subject during a sleep session with a detection system. The system comprises one or more sensors, one or more physical computer processors, and/or other components. The method comprises generating, with the one or more sensors, output signals conveying information related to brain activity of the subject; detecting, with the one or more physical computer processors, individual sleep stages of the subject during the sleep session based on the output signals, the individual sleep stages including a deep sleep stage; and responsive to detecting the deep sleep stage: generating, with the one or more physical computer processors, a harmonic representation of the output signals for a period of time during the sleep session that includes the deep sleep stage; identifying, with the one or more physical computer processors, two or more points of significance on the harmonic representation of the output signals; and analyzing, with the one or more physical computer processors, a shape of the harmonic representation of the output signals around the two or more points of significance to determine whether the shape of the harmonic representation of the output signals around the two or more points of significance corresponds to a shape of a slow wave.

Still another aspect of the present disclosure relates to a system configured to detect slow waves in a subject during a sleep session. The system comprises means for generating output signals conveying information related to brain activity of the subject; means for detecting individual sleep stages of the subject during the sleep session based on the output signals, the individual sleep stages including a deep sleep stage; and, responsive to detecting the deep sleep stage: means for generating a harmonic representation of the output signals for a period of time during the sleep session that includes the deep sleep stage; means for identifying two or more points of significance on the harmonic representation of the output signals; and means for analyzing a shape of the harmonic representation of the output signals around the two or more points of significance to determine whether the shape of the harmonic representation of the output signals around the two or more points of significance corresponds to a shape of a slow wave.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
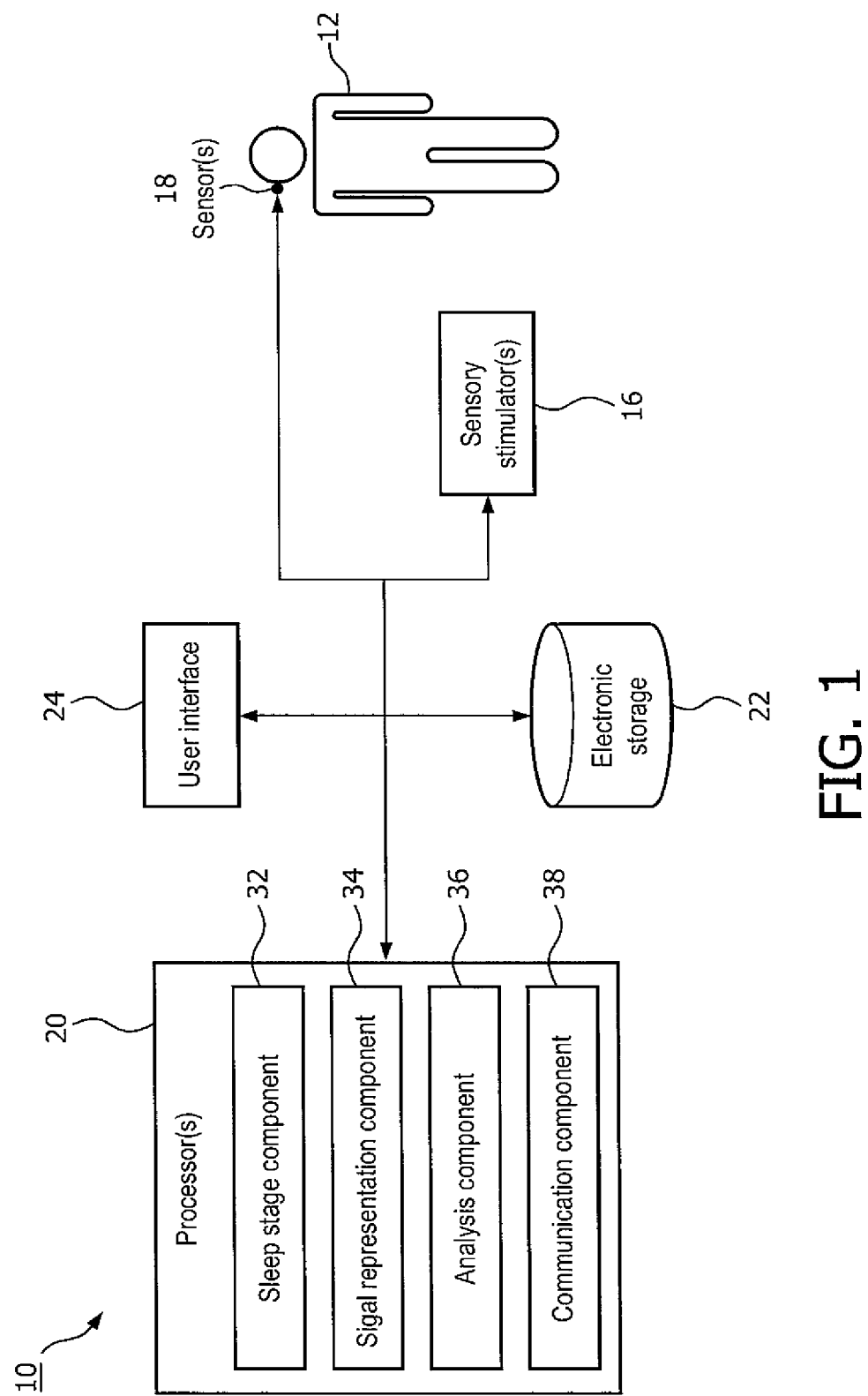
FIG. 1 is a schematic illustration of a system configured to detect slow waves in a subject during a sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to detect slow waves in a subject 12 during a sleep session. System 10 is a computationally uncomplicated and relatively inexpensive system that provides fast detection of slow waves in real time or near real time during the sleep session. In some embodiments, system 10 comprises one or more of a sensory stimulator 16, a sensor 18, a processor 20, electronic storage 22, a user interface 24, and/or other components.

System 10 is configured such that a current sleep stage of subject 12 is detected one or more times during the sleep session. In some embodiments, system 10 is configured to provide sensory stimuli to subject 12 during the sleep session based on output signals generated by sensor 18, slow waves detected by processor 20, and/or other information. System 10 is configured such that the delivery of sensory stimulation during the sleep session induces slow waves and/or adjusts (e.g., enhance and/or decrease) slow wave activity (SWA) in subject 12. The delivery of the sensory stimulation is timed to correspond to the detected slow waves.

Sleep stages may include rapid eye movement (REM) sleep, and/or non-rapid eye movement (NREM) stage N1, stage N2, and/or stage N3 sleep. In some embodiments, stage N3 sleep may be and/or correspond to deep and/or slow wave sleep. In some embodiments, stage N2 and/or stage N3 sleep may be deep and/or slow wave sleep. In some embodiments, slow waves may not be present throughout the whole N3 period, for example, but it may be significantly more likely that such slow waves are present during N3. Slow waves may also be present (although to a lesser extent) during N2, for example. System 10 is configured to detect such slow waves in real time and/or near real time. Deep and/or slow wave sleep and/or SWA may be observed and/or estimated by way of an electroencephalogram (EEG), and/or by other methods.

System 10 is configured to digitally filter and then decompose a frontal EEG signal to identify slow waves during a sleep session of subject 12. System 10 removes the direct current (0 Hz) component of the EEG signal with a digital high pass filter, removes noisy components of the EEG signal above about 18 Hz with a low pass filter, and then monitors for a substantially V shaped signal that has an amplitude that exceeds a pre-determined amplitude threshold (e.g., about 40 µV).

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, a headset (not shown) worn by subject 12 may include sensing electrodes (e.g., sensor 18), a wireless audio device (e.g., sensory stimulator 16), one or more processors (e.g., processor 20), and/or other components.

Sensory stimulator 16 is configured to provide sensory stimuli to subject 12. Sensory stimulator 16 is configured to provide sensory stimuli to subject 12 prior to a sleep session, during a sleep session, and/or at other times. For example, sensory stimulator 16 may be configured to provide sensory stimuli to subject 12 that correspond to slow waves detected during the sleep session. In some embodiments, sensory stimulator 16 may be configured to provide sensory stimulation through non-invasive brain stimulation and/or other methods. Sensory stimulator 16 may be configured to provide sensory stimulation through non-invasive brain stimulation using sensory stimuli such as odors, sounds, visual stimulation, touches, tastes, and/or other stimuli. For example, sensory stimulator 16 may be configured to provide auditory stimulation (e.g., audible tones) to subject 12 that correspond to detected slow waves. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to generate output signals conveying information related to brain activity of subject 12 and/or other information. In some embodiments, sensor 18 is configured such that the output signals are associated with a frontal EEG. Sensor 18 may comprise one or more sensors that generate such information directly. For example, sensor 18 may include electrodes configured to detect electrical activity along the scalp of subject 12 resulting from current flows within the brain of subject 12. Sensor 18 may comprise one or more sensors that generate output signals conveying information related to the brain activity of subject 12 indirectly. For example, one or more sensors 18 may generate an output based on a heart rate of subject 12 (e.g., sensor 18 may be a heart rate sensor located on the chest of subject 12, and/or be configured as an optical sensor included in a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), changes in skin color of subject 12 (e.g., sensor 18 may include a camera that can detect changes is skin color of subject 12 and infer vital signs such as heart rate, breathing rate, and/or other vital signs from the changes in color), respiration of subject 12, and/or other characteristics of subject 12. Although sensor 18 is illustrated at a single location in communication with subject 12, this is not intended to be limiting. Sensor 18 may include sensors disposed in a plurality of locations, such as for example, within (or in communication with) sensory stimulator 16, and/or in other locations.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24), or processor 20 may represent processing functionality of a plurality of devices operating in coordination.

As shown in FIG. 1, processor 20 is configured to execute one or more computer program components. The one or more computer program components may comprise one or more of a sleep stage component 32, a signal representation component 34, an analysis component 36, a communication component 38, and/or other components. Processor 20 may be configured to execute components 32, 34, 36, and/or 38 by software; hardware; firmware; some combination of software, hardware, and/or firmware; and/or other mechanisms for configuring processing capabilities on processor 20.

It should be appreciated that although components 32, 34, 36, and 38 are illustrated in FIG. 1 as being co-located within a single processing unit, in embodiments in which processor 20 comprises multiple processing units, one or more of components 32, 34, 36, and/or 38 may be located remotely from the other components. The description of the functionality provided by the different components 32, 34, 36, and/or 38 described below is for illustrative purposes, and is not intended to be limiting, as any of components 32, 34, 36, and/or 38 may provide more or less functionality than is described. For example, one or more of components 32, 34, 36, and/or 38 may be eliminated, and some or all of its functionality may be provided by other components 32, 34, 36, and/or 38. As another example, processor 20 may be configured to execute one or more additional components that may perform some or all of the functionality attributed below to one of components 32, 34, 36, and/or 38.

Sleep stage component 32 is configured to detect individual sleep stages of subject 12 during the sleep session. Sleep stage component 32 is configured to detect the individual sleep stages based on the output signals from sensor 18 and/or other information. As described above, the sleep stage of subject 12 may correspond to one or more of wakefulness, REM sleep, stage N1, stage N2, and/or stage N3 sleep. In some embodiments, the individual sleep stages include a deep sleep stage. In some embodiments, deep sleep, slow wave sleep, and/or slow wave activity may correspond to stage N3 sleep. In some embodiments, stage N2 and/or stage N3 sleep may be deep sleep and/or slow wave sleep and/or may correspond to deep sleep and/or slow wave activity. In some embodiments, sleep stage component 32 is configured such that detecting individual sleep stages includes selecting a sleep stage from the set of potential sleep stages (e.g., wakefulness, REM, N1, N2, N3), wherein the set of potential sleep stages includes the deep sleep stage.

In some embodiments, sleep stage module 32 may determine the current sleep stage of subject 12 based on an analysis of the information conveyed by the output signals of sensor 18. The analysis may include generating and/or monitoring an EEG during the sleep session of subject 12. In some embodiments, the analysis may include detecting slow wave sleep based on a power in a delta band and/or a power in a beta band of the EEG, and/or other information.

Signal representation component 34 is configured to, responsive to sleep stage component 32 detecting the deep sleep stage, generate a harmonic representation of the output signals for a period of time during the sleep session that includes the deep sleep stage and identify two or more points of significance on the harmonic representation of the output signals. In some embodiments, the harmonic representation of the output signals is a harmonic representation of EEG voltage that is indicative of brain activity of subject 12 during the sleep session, and/or other brain activity information conveyed by the output signals.

Figure 2:
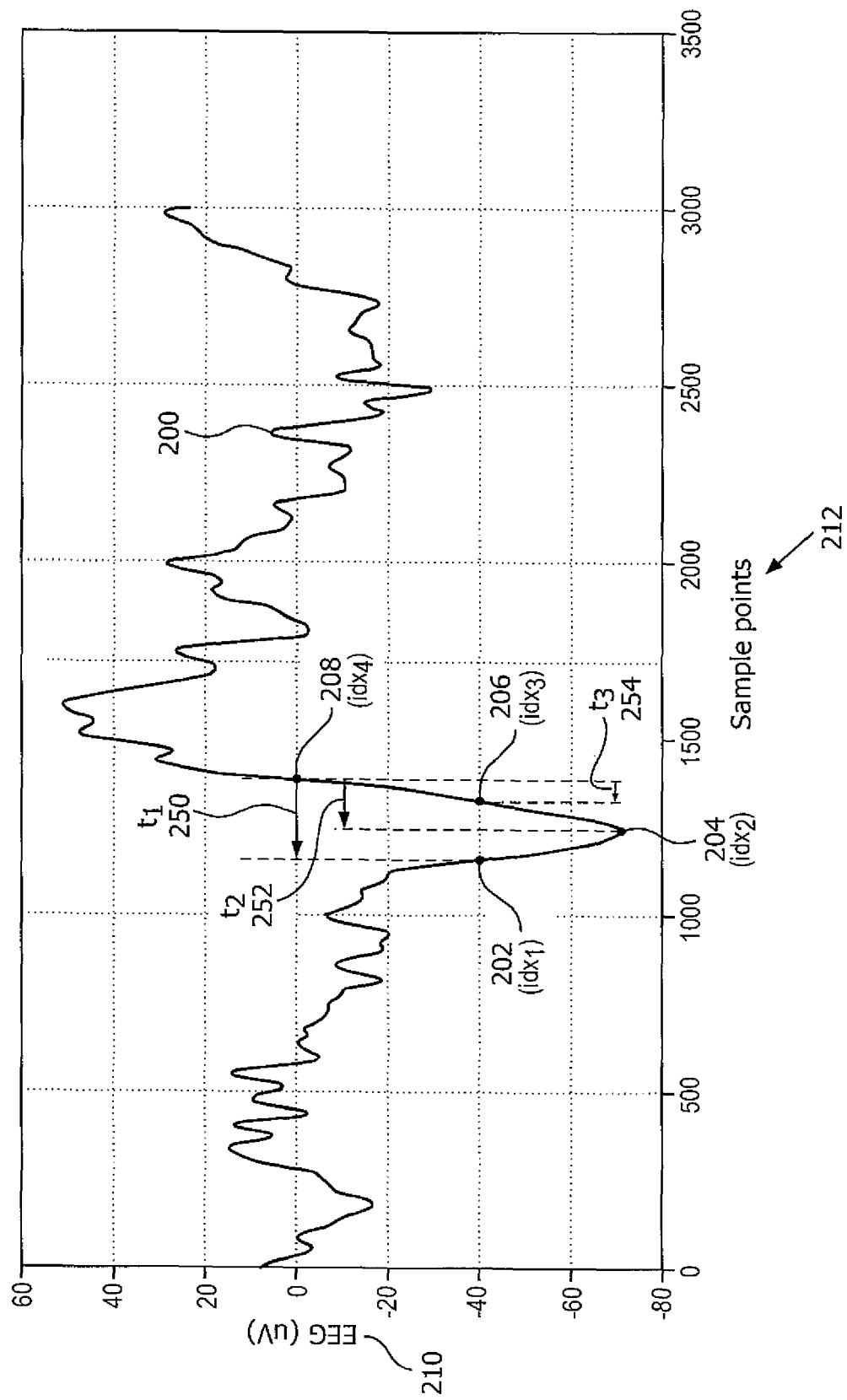
FIG. 2 illustrates a harmonic representation of EEG voltage with four points of significance identified.

By way of a non-limiting example, signal representation component 34 may be configured such that four points of significance are identified. FIG. 2 illustrates such an example. FIG. 2 illustrates a harmonic representation 200 of EEG voltage with four points of significance 202 ($idx_1$), 204 ($idx_2$), 206 ($idx_3$), and 208 ($idx_4$) identified. In FIG. 2, EEG voltage 200 is plotted in micro volts (µV) 210 over time 212 (1000 sample points is 1 second). The four points of significance 202, 204, 206, and 208 shown in FIG. 2 include, for example, a first point of significance 202 at a first negative crossing of voltage 200 over −40 µV, a second point of significance 204 at a local minimum of voltage 200 after the first negative crossing −40 µV, a third point of significance 206 at a first positive crossing of voltage 200 over −40 µV after the local minimum, and fourth point of significance 208 at a first positive crossing of voltage 200 over 0V after the local minimum.

These specific points of significance are not intended to be limiting. For example, instead of −40 µV, signal representation component 34 may be configured to determine points of significance that correspond to any voltage between about −35 µV and about −45 µV. In some embodiments, signal representation component 34 may be configured to determine points of significance that correspond to any voltage between about −20 µV and about −60 µV.

Returning to FIG. 1, analysis component 36 is configured to analyze a shape of the harmonic representation of the output signals around the points of significance to determine whether the shape of the harmonic representation of the output signals around points of significance corresponds to a shape of a slow wave.

Figure 3:
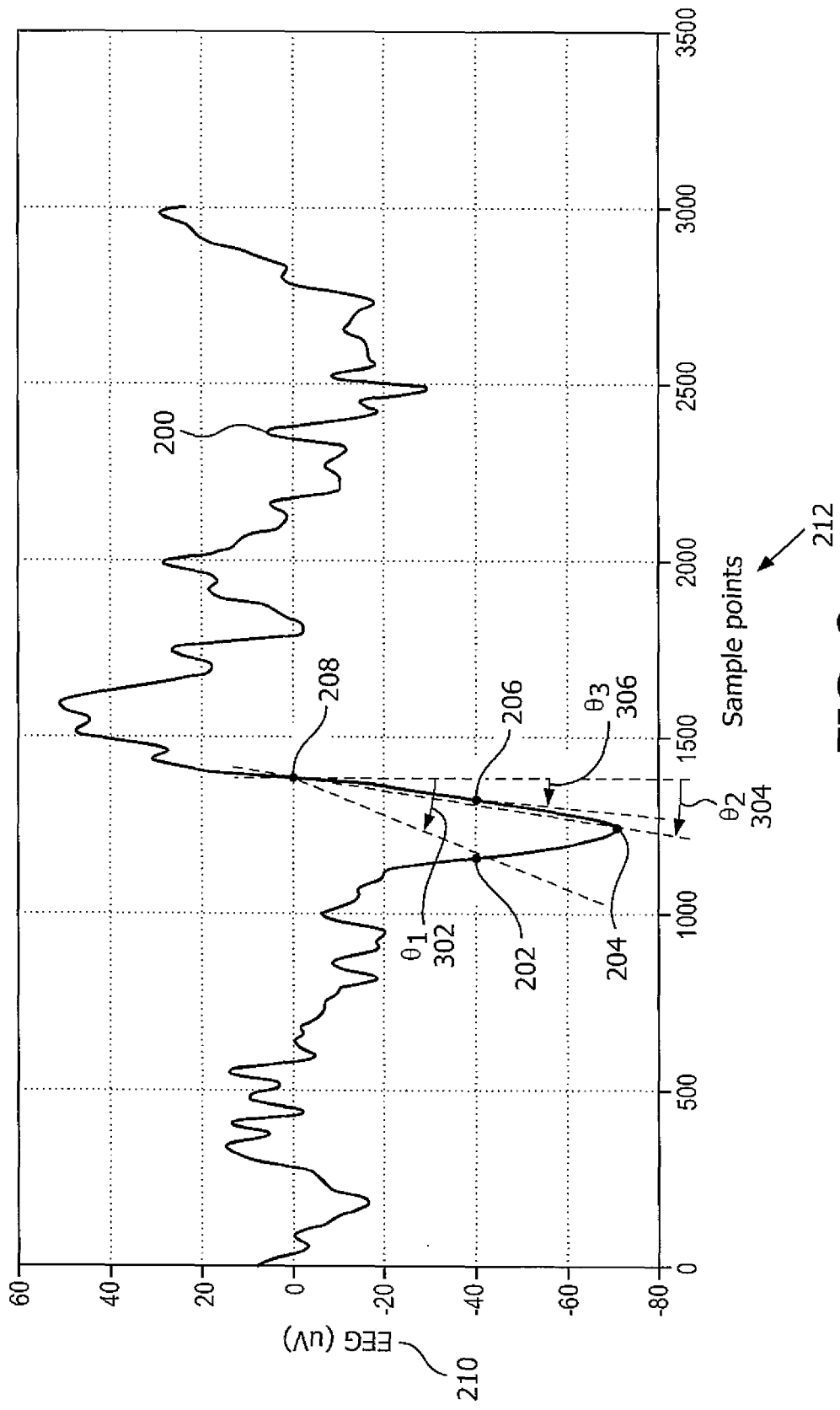
FIG. 3 illustrates angular deflections that correspond to the points of significance.

In some embodiments, analysis component 36 is configured such that analyzing the shape of the harmonic representation of the output signals includes determining angular deflections of the points of significance. Continuing with the non-limiting example described above and shown in FIG. 2, the angular deflections may include a first angular deflection ($\theta_1$) of voltage 200 at first point of significance 202, a second angular deflection ($\theta_2$) of voltage 200 at second point of significance 204, and a third angular deflection ($\theta_3$) of voltage 200 at third point of significance 206. The angular deflection ($\theta_4$) of fourth point of significance 208 may be assumed to be zero. FIG. 3 illustrates angular deflections 302 ($\theta_1$), 304 ($\theta_2$), 306 ($\theta_3$), that correspond to the points of significance 202, 204, 206. The angular deflections that correspond to the points of significance may be determined as follows:

$$\theta_1 = \pi - \sin^{-1}\frac{-40}{\text{Min}};$$

$$\theta_2 = \pi/2;$$

$$\theta 3 = \sin^{-1} \frac{-40}{\text{Min}}; \text{ and}$$

$$\theta = 0 \text{ (assumed)}.$$

In some embodiments, analysis component 36 (FIG. 1) is configured such that analyzing the shape of the harmonic representation of the output signals includes determining amounts of time between the points of significance. Continuing with the non-limiting example above and shown in FIG. 2 and FIG. 3, the amounts of time may include a first amount of time ($t_1$) 250 (shown in FIG. 2) between fourth point of significance 208 and first point of significance 202, a second amount of time ($t_2$) 252 between fourth point of significance 208 and second point of significance 204, and a third amount of time ($t_3$) 254 between fourth point of significance 208 and third point of significance 208. These amounts of time may be expressed (in seconds for example) as (1000 sample points is 1 second):

$$t1 = \frac{idx4 - idx1}{1000}$$

$$t2 = \frac{idx4 - idx2}{1000}; \text{ and}$$

$$t3 = \frac{idx4 - idx3}{1000}.$$

Figure 4:
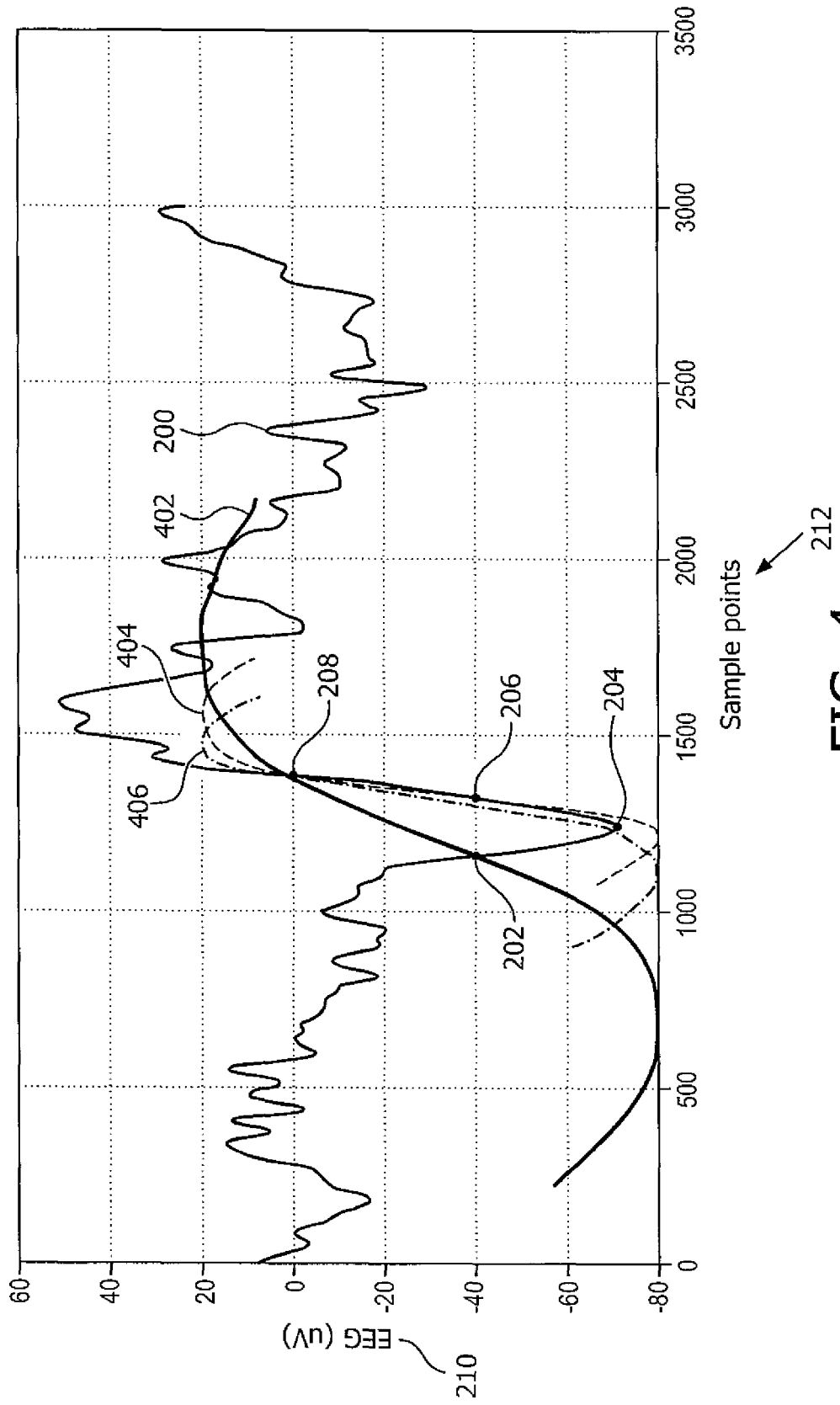
FIG. 4 illustrates three sine waves of equal amplitude that pass through the points of significance.

In some embodiments, analysis component 36 (FIG. 1) is configured such that analyzing the shape of the harmonic representation of the output signals includes determining frequencies of sine waves of equal amplitude that pass through the points of significance based on the angular deflections and the amounts of time. Continuing with the non-limiting example described above and in FIG. 2 and FIG. 3, FIG. 4 illustrates three sine waves 402, 404, 406 of equal amplitude that pass through the points of significance. The determined frequencies may include a first frequency ($\omega_1$) of a first sine wave 402 that passes through first point of significance 202 and fourth point of significance 208 determined based on first angular deflection ($\theta_1$) 302 (FIG. 3) and first amount of time ($t_1$) 250 (FIG. 2), a second frequency ($\omega_2$) of a second sine wave 404 that passes through second point of significance 204 and fourth point of significance 208 determined based on second angular deflection ($\theta_2$) 304 (FIG. 3) and second amount of time ($t_2$) 252 (FIG. 2), and a third frequency ($\omega_3$) of a third sine wave 406 that passes through third point of significance 206 and fourth point of significance 208 determined based on third angular deflection ($\theta_3$) 306 and third amount of time ($t_3$) 254. In short, the three frequencies ($\omega k$) may be given by the assumed angular displacement over time ($\omega k = \theta k/tk$).

In some embodiments, analysis component 36 (FIG. 1) is configured such that analyzing the shape of the harmonic representation of the output signals includes determining an average frequency based on the frequencies of the sine waves that pass through the points of significance. Continuing with the non-limiting example described above and shown in FIG. 2-FIG. 4, the average frequency may be determined based on the equation $\omega=(\omega_1+\omega_2+\omega_3)/3$. Analysis component 36 is configured to compare the average frequency to a slow wave frequency range, and, responsive to the average frequency being within the slow wave frequency range, detect a slow wave. In some embodiments, the slow wave frequency range may between about 0.5 Hz and about 2 Hz. In some embodiments, the slow wave frequency range may between about 2 Hz and about 4 Hz. In some embodiments, the slow wave frequency range may between about 0.5 Hz and about 4 Hz. For example, during N3 sleep (e.g., detected by sleep stage component 32), if $\omega$ is between $\pi/2$ and $4\pi$ (about 0.5 to about 2 Hz), then a slow wave may be detected. In some embodiments, the slow wave frequency range may be programmed at manufacture, set by a user via user interface 24, determined by system 10 based on previous sleep sessions of subject 12, determined based on the current sleep session, and/or determined by other methods.

In some embodiments, analysis component 36 is configured such that analyzing the shape of the harmonic representation of the voltage (for example) includes comparing a deep sleep segment of the EEG to a reference waveform. For example, in addition to and/or instead of the analysis described in the non-limiting example above, analysis component 36 may be configured to identify candidate slow-wave EEG segments ($V_{cand}$) in real-time; condition the candidate waveforms, for example, via normalization and/or decimation; and classify the candidate waveforms (e.g., as either slow waves or not slow waves) via numerical bounds on the output of $f(V_{cand}, V_{ref})$, which is a function of both the candidate waveform, and a reference waveform ($V_{ref}$), which is determined empirically and/or via manual construction. In some embodiments, the numerical bounds may be programmed at manufacture, set by a user via user interface 24, determined by system 10 based on previous sleep sessions of subject 12, determined based on the current sleep session, and/or determined by other methods. Three possible embodiments of $f(V_{cand}, V_{ref})$ include:

$$f(V_{cand}, V_{ref}) = \mu = \text{mean}(|V_{cand} - V_{ref}|);$$

$$f(V_{cand}, V_{ref}) = \sigma = std(V_{cand} - V_{ref}); \text{ and}$$

$$f(V_{cand}, V_{ref}) = \mu * \sigma = \text{mean}(|V_{cand} - V_{ref}|) * std(V_{cand} - V_{ref}).$$

Advantages of this type of analysis by analysis component 36 include early detection of slow waves (e.g., at or near the negative peak 204 shown in FIG. 2), and not rejecting false-positives which do not exhibit slow-wave morphology and shape. This method allows early morphological detection at or near the negative peak (e.g., point of significance 204). A reference template, and numerical bounds on $f(V_{cand}, V_{ref})$ may be selected to fit the needs of the application.

In some embodiments, analysis component 36 is configured such that analyzing the shape of the harmonic representation of the output signals (e.g., voltage) includes determining one or more slopes of the harmonic representation of the output signals around the points of significance. For example, in addition to and/or instead of the analysis described above, analysis component 36 may be configured such that voltage signal 200 (FIG. 2) is assumed to be a monotonic sine wave. A frequency of voltage signal 200 may be determined by estimating the rate of change (e.g., the slope) at one or more points along voltage signal 200. For example, the slope of voltage signal 200 at a zero crossing (e.g., point of significance 208 shown in FIG. 2) may be an approximation of angular frequency (e.g., because a derivative of $\sin(\omega t)$ at $t=0$, is $\omega$.) Then, estimating the difference in rates of change (e.g., the slopes) of voltage signal 200 before and after a negative peak (e.g., point of significance 204 shown in FIG. 2), provides an approximation of the square of the angular frequency (e.g., because the second derivative of $\sin(\omega t)$ at $t=-\pi/(2\omega)$, which is $\omega^2$.) Analysis component 36 may then be configured to compare the determined frequency to a slow wave frequency range, and, responsive to the determined frequency being within the slow wave frequency range, detect a slow wave.

Returning to FIG. 1, communication component 38 is configured to control sensory stimulator 16 to provide the sensory stimuli to subject 12 during the individual time periods of slow wave sleep (e.g., during stage N3 sleep). The timing for delivery of sensory stimulation corresponds to the detection of slow waves in subject 12 (e.g., by analysis component 36). In some embodiments, communication component 38 is configured to control sensory stimulator 16 to provide the sensory stimuli in the form of auditory tones, and/or other stimuli. In some embodiments, characteristics of the sensory stimuli (e.g., auditory tone volume, duration, etc.) may be programmed at manufacture, set by a user via user interface 24, determined by system 10 based on previous sleep sessions of subject 12, determined based on the current sleep session, and/or determined by other methods. In some embodiments, communication component 38 is configured to control sensory stimulator 16 to provide the sensory stimuli at an intensity level that does not wake subject 12.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or the other users may provide information to and receive information from system 10. Other users may include doctors, caregivers, and/or other users, for example. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 5:
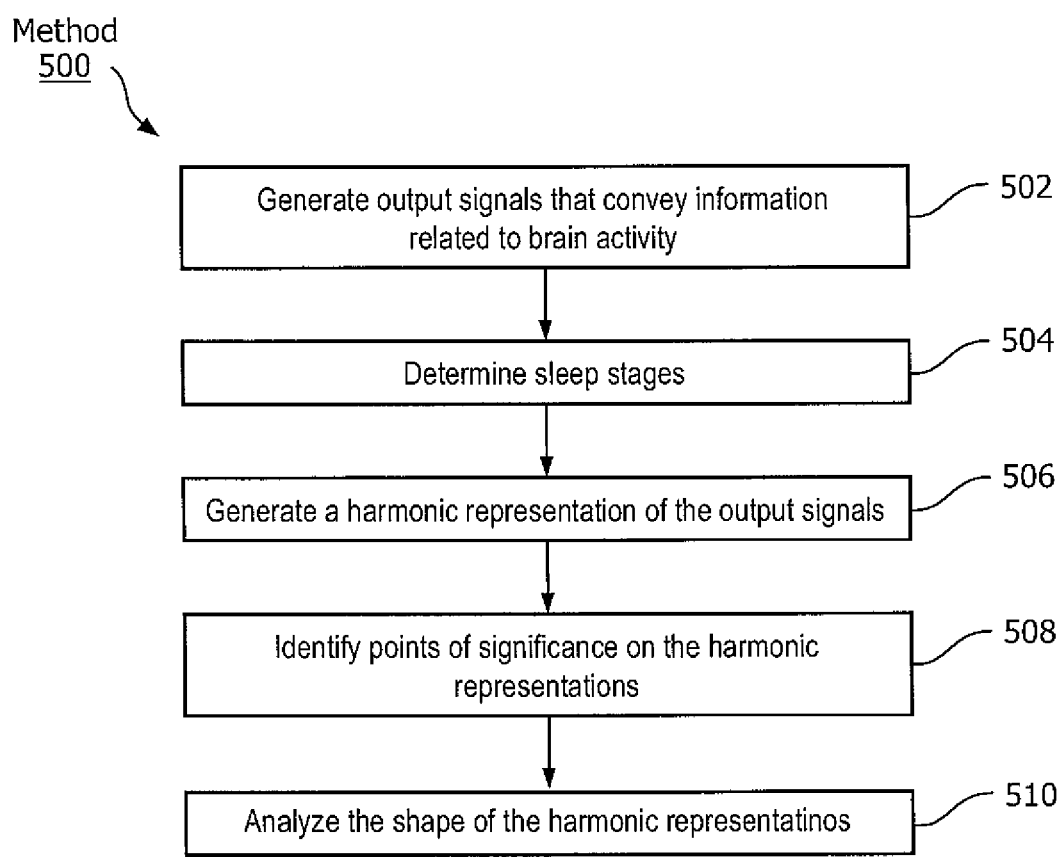
FIG. 5 illustrates a method for detecting slow waves in a subject during a sleep session with a detection system.

FIG. 5 illustrates a method for detecting slow waves in a subject during a sleep session with a detection system. The detection system comprises one or more sensors, one or more physical computer processors, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, output signals conveying information related to brain activity of the subject during the sleep session are generated. In some embodiments, the output signals are associated with a frontal electroencephalogram (EEG). In some embodiments, operation 502 is performed by one or more sensors the same as or similar to sensors 18 (shown in FIG. 1 and described herein).

At an operation 504, individual sleep stages of the subject are determined based on the output signals. The individual sleep stages include a deep sleep stage. In some embodiments, operation 504 is performed by a physical computer processor the same as or similar to processor 20 (shown in FIG. 1 and described herein).

At an operation 506, responsive to detecting the deep sleep stage, a harmonic representation of the output signals for a period of time during the sleep session that includes the deep sleep stage is generated. In some embodiments, the harmonic representation of the output signals is a harmonic representation of voltage. In some embodiments, operation 506 is performed by a physical computer processor the same as or similar to processor 20 (shown in FIG. 1 and described herein).

At an operation 508, two or more points of significance on the harmonic representation of the output signals are identified. In some embodiments, four points of significance are identified. The four points of significance include a first point of significance at a first negative crossing of the voltage over −40 μV, a second point of significance at a local minimum of the voltage after the first negative crossing, a third point of significance at a first positive crossing of the voltage over −40 μV after the local minimum, and fourth point of significance at a first positive crossing of the voltage over 0V after the local minimum. In some embodiments, operation 508 is performed by a physical computer processor the same as or similar to processor 20 (shown in FIG. 1 and described herein).

At an operation 510, a shape of the harmonic representation of the output signals around the two or more points of significance is analyzed to determine whether the shape of the harmonic representation of the output signals around the two or more points of significance corresponds to a shape of a slow wave.

In some embodiments, analyzing the shape of the harmonic representation of the voltage includes determining angular deflections of the voltage at the points of significance. The angular deflections include a first angular deflection of the voltage at the first point of significance, a second angular deflection of the voltage at the second point of significance, and a third angular deflection of the voltage at the third point of significance. Analyzing may include determining amounts of time between the points of significance. The amounts of time include a first amount of time between the fourth point of significance and the first point of significance, a second amount of time between the fourth point of significance and the second point of significance, and a third amount of time between the fourth point of significance and the third point of significance. Analyzing may include determining frequencies of sine waves that pass through the points of significance based on the angular deflections and the amounts of time. The frequencies include a first frequency of a first sine wave that passes through the first point of significance and the fourth point of significance determined based on the first angular deflection and the first amount of time, a second frequency of a second sine wave that passes through the second point of significance and the fourth point of significance determined based on the second angular deflection and the second amount of time, and a third frequency of a third sine wave that passes through the third point of significance and the fourth point of significance determined based on the third angular deflection and the third amount of time. Analyzing may include determining an average frequency based on the frequencies of the sine waves that pass through the points of significance, comparing the average frequency to a slow wave frequency range, and, responsive to the average frequency being within the slow wave frequency range, detecting a slow wave.

In some embodiments, analyzing the shape of the harmonic representation of voltage includes comparing a deep sleep segment of the electroencephalogram to a reference waveform. In some embodiments, analyzing the shape of the harmonic representation of the output signals includes determining a slope of the harmonic representation of the output signals around the two or more points of significance.

In some embodiments, operation 510 is performed by a physical computer processor the same as or similar to processor 20 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to detect slow waves in a subject during a sleep session, the system comprising:
   a sensory stimulator configured to provide sensory stimulation to the subject to enhance sleep of the subject during the sleep session;
   one or more sensors configured to generate output signals conveying information related to brain activity of the subject; and
   one or more physical computer processors configured by computer-readable instructions to:
      detect individual sleep stages of the subject during the sleep session based on the output signals, the individual sleep stages including a deep sleep stage; and
      responsive to detecting the deep sleep stage:
         generate a harmonic representation of the output signals for a period of time during the sleep session that includes the deep sleep stage;
         identify points of significance on the harmonic representation of the output signals, wherein the harmonic representation of the output signals is a harmonic representation of voltage, and wherein the points of significance include a first point of significance at a first negative crossing of a first voltage, a second point of significance at a local minimum of the voltage after the first negative crossing, a third point of significance at a first positive crossing of a second voltage after the local minimum, and a fourth point of significance at a first positive crossing of the voltage at 0V after the local minimum, wherein the first voltage is between about −20 μV and about −60 μV and the second voltage is between about −20 μV and about −60 μV;
         analyze a shape of the harmonic representation of the output signals around the points of significance to determine whether the shape of the harmonic representation of the output signals around the points of significance corresponds to a shape of a slow wave; and
         responsive to determining the shape of the harmonic representation of the output signals around the points of significance corresponds to the shape of the slow wave, control the sensory stimulator to provide the sensory stimulation to the subject.

2. The system of claim 1, wherein the one or more physical computer processors are configured such that:
   the first point of significance is at the first negative crossing of the voltage at −40 μV, and the third point of significance is at the first positive crossing of the voltage at −40 μV after the local minimum;

wherein analyzing the shape of the harmonic representation of the voltage includes:
determining angular deflections of the voltage at the points of significance, the angular deflections including a first angular deflection of the voltage from the fourth point of significance to the first point of significance, a second angular deflection of the voltage from the fourth point of significance to the second point of significance, and a third angular deflection of the voltage from the fourth point of significance to the third point of significance;
determining amounts of time between the points of significance, the amounts of time including a first amount of time between the fourth point of significance and the first point of significance, a second amount of time between the fourth point of significance and the second point of significance, and a third amount of time between the fourth point of significance and the third point of significance;
determining frequencies of sine waves that pass through the points of significance within a single period of a given sine wave based on the angular deflections and the amounts of time, the frequencies including a first frequency of a first sine wave that passes through the first point of significance and the fourth point of significance in a single period of the first sine wave determined based on the first angular deflection and the first amount of time, a second frequency of a second sine wave that passes through the second point of significance and the fourth point of significance in a single period of the second sine wave determined based on the second angular deflection and the second amount of time, and a third frequency of a third sine wave that passes through the third point of significance and the fourth point of significance in a single period of the third sine wave determined based on the third angular deflection and the third amount of time;
determining an average frequency based on the frequencies of the sine waves that pass through the points of significance;
comparing the average frequency to a slow wave frequency range; and
responsive to the average frequency being within the slow wave frequency range, detecting the slow wave.

3. The system of claim 1, wherein the one or more sensors are configured such that the output signals are associated with a frontal electroencephalogram (EEG).

4. The system of claim 3, wherein, the one or more physical computer processors are configured such that:
analyzing the shape of the harmonic representation of voltage includes comparing a deep sleep segment of the electroencephalogram to a reference waveform.

5. The system of claim 1, wherein the one or more physical computer processors are configured such that analyzing the shape of the harmonic representation of the output signals includes determining individual slopes of sections of the harmonic representation of the output signals around the points of significance.

6. A method for detecting slow waves in a subject during a sleep session with a detection system, the system comprising one or more sensors and one or more physical computer processors, the method comprising:
generating, with the one or more sensors, output signals conveying information related to brain activity of the subject;
detecting, with the one or more physical computer processors, individual sleep stages of the subject during the sleep session based on the output signals, the individual sleep stages including a deep sleep stage; and
responsive to detecting the deep sleep stage:
generating, with the one or more physical computer processors, a harmonic representation of the output signals for a period of time during the sleep session that includes the deep sleep stage;
identifying, with the one or more physical computer processors, points of significance on the harmonic representation of the output signals, wherein the harmonic representation of the output signals is a harmonic representation of voltage, and wherein the points of significance include a first point of significance at a first negative crossing of a first voltage, a second point of significance at a local minimum of the voltage after the first negative crossing, a third point of significance at a first positive crossing of a second voltage after the local minimum, and a fourth point of significance at a first positive crossing of the voltage at 0V after the local minimum;
analyzing, with the one or more physical computer processors, a shape of the harmonic representation of the output signals around the points of significance to determine whether the shape of the harmonic representation of the output signals around the points of significance corresponds to a shape of a slow wave; and
responsive to determining the shape of the harmonic representation of the output signals around the points of significance corresponds to the shape of the slow wave, controlling a sensory stimulator to provide sensory stimulation to the subject.

7. The method of claim 6, wherein the one or more physical computer processors are configured such that:
the first point of significance is at the first negative crossing of the voltage at $-40$ μV, and the third point of significance is at the first positive crossing of the voltage at $-40$ μV after the local minimum;
wherein analyzing the shape of the harmonic representation of the voltage includes:
determining angular deflections of the voltage at the points of significance, the angular deflections including a first angular deflection of the voltage from the fourth point of significance to the first point of significance, a second angular deflection of the voltage from the fourth point of significance to the second point of significance, and a third angular deflection of the voltage from the fourth point of significance to the third point of significance;
determining amounts of time between the points of significance, the amounts of time including a first amount of time between the fourth point of significance and the first point of significance, a second amount of time between the fourth point of significance and the second point of significance, and a third amount of time between the fourth point of significance and the third point of significance;
determining frequencies of sine waves that pass through the points of significance within a single period of a given sine wave based on the angular deflections and the amounts of time, the frequencies including a first frequency of a first sine wave that passes through the first point of significance and the fourth point of significance in a single period of the first sine wave determined based on the first angular deflection and the first amount of time, a second frequency of a second sine wave that passes through the second point of significance and the fourth point of significance in a single period of the second sine wave determined based on the second angular deflection and the second amount of time, and a third frequency of a third sine wave that passes through the third point of significance and the fourth point of significance in a single period of the third sine wave determined based on the third angular deflection and the third amount of time;

determining an average frequency based on the frequencies of the sine waves that pass through the points of significance;

comparing the average frequency to a slow wave frequency range; and responsive to the average frequency being within the slow wave frequency range, detecting the slow wave.

8. The method of claim 6, wherein the output signals are associated with a frontal electroencephalogram (EEG).

9. The method of claim 8, wherein: analyzing the shape of the harmonic representation of voltage includes comparing a deep sleep segment of the electroencephalogram to a reference waveform.

10. The method of claim 6, wherein analyzing the shape of the harmonic representation of the output signals includes determining individual slopes of sections of the harmonic representation of the output signals around the points of significance.

11. A system configured to detect slow waves in a subject during a sleep session, the system comprising:

means for providing sensory stimulation to the subject to enhance sleep of the subject during the sleep session;

means for generating output signals conveying information related to brain activity of the subject;

means for detecting individual sleep stages of the subject during the sleep session based on the output signals, the individual sleep stages including a deep sleep stage; and responsive to detecting the deep sleep stage:

means for generating a harmonic representation of the output signals for a period of time during the sleep session that includes the deep sleep stage;

means for identifying points of significance on the harmonic representation of the output signals wherein the harmonic representation of the output signals is a harmonic representation of voltage, and wherein the points of significance include a first point of significance at a first negative crossing of a first voltage, a second point of significance at a local minimum of the voltage after the first negative crossing, a third point of significance at a first positive crossing of a second voltage after the local minimum, and a fourth point of significance at a first positive crossing of the voltage at 0V after the local minimum;

means for analyzing a shape of the harmonic representation of the output signals around the points of significance to determine whether the shape of the harmonic representation of the output signals around the points of significance corresponds to a shape of a slow wave; and means for, responsive to determining the shape of the harmonic representation of the output signals around the points of significance corresponds to the shape of the slow wave, controlling the means for providing sensory stimulation to provide sensory stimulation to the subject.

12. The system of claim 11, wherein the means for identifying the points of significance are configured such that the first point of significance is at the first negative crossing of the voltage at −40 μV, and the third point of significance is at the first positive crossing of the voltage at −40 μV after the local minimum;

wherein the means for analyzing are configured such that analyzing the shape of the harmonic representation of the voltage includes:

determining angular deflections of the voltage at the points of significance, the angular deflections including a first angular deflection of the voltage from the fourth point of significance to the first point of significance, a second angular deflection of the voltage from the fourth point of significance to the second point of significance, and a third angular deflection of the voltage from the fourth point of significance to the third point of significance;

determining amounts of time between the points of significance, the amounts of time including a first amount of time between the fourth point of significance and the first point of significance, a second amount of time between the fourth point of significance and the second point of significance, and a third amount of time between the fourth point of significance and the third point of significance;

determining frequencies of sine waves that pass through the points of significance within a single period of a given sine wave based on the angular deflections and the amounts of time, the frequencies including a first frequency of a first sine wave that passes through the first point of significance and the fourth point of significance in a single period of the first sine wave determined based on the first angular deflection and the first amount of time, a second frequency of a second sine wave that passes through the second point of significance and the fourth point of significance in a single period of the second sine wave determined based on the second angular deflection and the second amount of time, and a third frequency of a third sine wave that passes through the third point of significance and the fourth point of significance in a single period of the third sine wave determined based on the third angular deflection and the third amount of time;

determining an average frequency based on the frequencies of the sine waves that pass through the points of significance;

comparing the average frequency to a slow wave frequency range; and responsive to the average frequency being within the slow wave frequency range, detecting the slow wave.

* * * * *